United States Patent [19]

Tanaka et al.

[11] Patent Number: 5,128,375
[45] Date of Patent: Jul. 7, 1992

[54] KELOID TREATING AGENT

[75] Inventors: Masaya Tanaka, Kobe; Masanori Nakata, Odawara; Hidejiro O'ya, Kyoto, all of Japan

[73] Assignee: Kanebo, Ltd., Tokyo, Japan

[21] Appl. No.: 645,251

[22] Filed: Jan. 24, 1991

[30] Foreign Application Priority Data

Feb. 1, 1990 [JP] Japan .................................. 2-22707

[51] Int. Cl.⁵ .............................................. A61K 31/13
[52] U.S. Cl. .................................................... 514/667
[58] Field of Search ........................................ 514/667

[56] References Cited

PUBLICATIONS

Chemical Abstracts, 96:210495y (1982).
Chemical Abstracts, 101:28194u (1984).
Byoin Yakkyoku Seizai, 2nd Edition, issued by Yakujinipposha, 1986, p. 56.
Japanese Patent Kokai 57520/1988 and Chemical Abstract, vol. 109, 1988, p. 66, 109:66895w.
Encyclopedia of Medical Sciences, vol. 14, p. 77, issued by Kodansha, 1982.
Biochemical and Biophysical Research Communications, vol. 121, No. 1, 1984, pp. 413-419.
Pharmazie, vol. 38, H, 7, pp. 488-489, 1983.
Nippon Nogeikagu Kaisha, vol. 59, No. 9, pp. 913-916, 1985.

Primary Examiner—Leonard Schenkman
Attorney, Agent, or Firm—Wegner, Cantor, Mueller & Player

[57] ABSTRACT

A keloid treating agent comprising as an active ingredient ethanolamine or a pharmaceutically acceptable salt thereof which is useful for the treatment of keloid such as true keloid, cicatrical keloid, hypertrophic scar, etc.

5 Claims, No Drawings

KELOID TREATING AGENT

TECHNICAL FIELD

The present invention relates to a keloid treating agent comprising as an essential active ingredient ethanolamine or a pharmaceutically acceptable salt thereof.

Keloid includes true keloid, cicatrical keloid, hypertrophic scar, etc. which are classified depending on the cause and symptoms thereof.

PRIOR ART

Ethanolamine or a pharmaceutically acceptable salt thereof has been used in the medical field as a sclerosing agent for sclerotherapy of esophageal varices (cf. Byoin Yakkyoku Seizai (Preparation in the medicine room of hospital), 2nd Edition, issued by Yakujinipposha in 1986, page 56). It is also known that ethanolamine or a pharmaceutically acceptable salt thereof has an anti-ulcer activity (cf. Japanese Patent First Publication (Kokai) No. 57520/1988). However, it has never been known that ethanolamine or a pharmaceutically acceptable salt thereof is useful for the treatment of keloid.

The treatment of keloid by a medicament has usually been done by application of a steroid drug to the keloid skin or by injection of a steroid drug into the keloid region. However, the former method, application of a steroid drug, is substantially not effective, and the latter method, injection of a steroid drug, is somewhat effective, but has drawbacks in that it is very painful upon injection and further that it is very difficult to inject an effective large amount of a steroid at one time, and hence it can not be applied to a large area keloid (cf. Encyclopedia of Medical Sciences, edited by Noma Koremichi, 14, 77, issued by Kodansha in 1982).

Keloid gives bad looks and further induces peculiar pain, pruritus, a feeling of hardened skin, a feeling of shrunken skin and the like, and hence, patients suffered from keloid anguish and have desired the development of an effective agent for treating keloid.

BRIEF DESCRIPTION OF THE INVENTION

The present inventors have extensively studied an improved agent useful for the treatment of keloid and have unexpectedly found that ethanolamine or a pharmaceutically acceptable salt thereof is effective for the treatment of keloid. Thus, the main object of the invention is to provide a keloid treating agent comprising as an active ingredient ethanolamine or a pharmaceutically acceptable salt thereof.

DETAILED DESCRIPTION OF THE INVENTION

The active ingredient in the keloid treating agent of the present invention is ethanolamine or a pharmaceutically acceptable salt thereof, such as inorganic salts (e.g. hydrochloride, sulfate, nitrate, etc.) or organic acid salts (e.g. acetate, citrate, fumarate, etc.).

The keloid treating agent of the present invention is usually used in the form of a pharmaceutical preparation such as ointments, gel preparations, creams, liquids, sprays, patches, lotions, and the like, which are percutaneously administered.

These preparations are prepared by conventional methods by using the active ethanolamine or a pharmaceutically acceptable salt thereof and a conventional pharmaceutically acceptable carrier or diluent, such as hydrocarbons (e.g. petrolatum, squalane, liquid paraffin, etc.), higher alcohols (e.g. stearyl alcohol, cetyl alcohol, etc.), higher fatty acid lower alkyl esters (e.g. isopropyl myristate, isopropyl palmitate, etc.), animal fats (e.g. lanolin, etc.), polyhydric alcohols (e.g. glycerin, propylene glycol, etc.), polyethylene glycols (e.g. macrogol 400, macrogol 4000, etc.), fatty acid esters of glycerin (e.g. glyceryl monostearate, etc.), surface active agents (e.g. sodium lauryl sulfate, polyethylene glycol monostearate, polyoxyethylene alkyl ether phosphate (tradename, NIKKOL DDP-2, manufactured by Nihon Surfactant Kogyo K.K.), etc.), waxes, resins, water and optionally preservatives (e.g. methyl parahydroxybenzoate, butyl parahydroxybenzoate, etc.).

The amount of ethanolamine or a pharmaceutically acceptable salt thereof in the preparations is not critical but is usually in the range of 0.01 to 20% by weight, preferably 0.05 to 5% by weight (as ethanolamine).

The dosage and usage of the keloid treating agent of the present invention may vary depending on the severity and state of the keloid, year duration of the keloid, age and weight of the patients, and the like, but it is usually used by percutaneous administration to the region of keloid or surrounding area thereof in a dose of 0.2 to 1000 $\mu g/cm^2$ (skin area) (as ethanolamine) per application. It is administered once to several times per day.

The keloid treating agent of the present invention is effective for improving or treating various symptoms of keloid by percutaneous administration (it has been clinically confirmed as shown Test 1 hereinafter). It was also been confirmed that the treating agent of the present invention is more effective than the conventional steroid drug (see Test 2 hereinafter). The active ingredient used in the present invention further exhibits excellent low skin irritation (see Test 3 hereinafter). Thus, the keloid treating agent of the present invention is very useful.

The effect and safety of the treating agent of the present invention is illustrated by the following tests.

Test 1

1. Test preparation:
The ointment of Example 1
2. Patient to be treated and administration method:

The patients were nine patients suffered from keloid who have been treated with a steroid ointment but have not sufficiently been treated thereby. The test preparation was applied to the skin of the keloid region and surrounding area thereof of these patients in an amount of 2 to 4 $\mu g/cm^2$ (skin area) (as an amount of ethanolamine) per once (applied to once a day). The sex and age of the patients, localization of keloid, year duration of keloid before initiation of the present treatment, administration frequency per a week, and the period of treatment are shown in Table 1.

TABLE 1

| Patient No. | Sex | Age | Localization of keloid | Year duration | Administ. frequency per week | Treatment period |
|---|---|---|---|---|---|---|
| 1 | Female | 2 | Left brachium | 2 | 4 | 1 month + 1 week |
| 2 | Female | 40 | Right finger | 3 | 4 | 1 month |
| 3 | Female | 13 | Right thigh | 8 | 3 | 2 months + 1 week |
| 4 | Female | 53 | Right foot | 2 | 4 | 1 month + 1 week |
| 5 | Female | 54 | Right | 1 | 4 | 1 month + |

TABLE 1-continued

| Patient No | Sex | Age | Localization of keloid | Year duration | Administ. frequency per week | Treatment period |
|---|---|---|---|---|---|---|
| | | | forearm | | | 1 week |
| 6 | Female | 8 | Left forearm | 5 | 3 | 3 months |
| 7 | Female | 8 | Right foot | 2 | 5 | 2 months + 1 week |
| 8 | Female | 74 | Right wrist | 3 | 4 | 3 months + 1 week |
| 9 | Male | 34 | Right abdomen | 2 | 7 | 7 months |

3. Evaluation of the therapeutic effects:

During the administration of the test preparation and 6 months after the final treatment (provided that as to the patient No. 9, 2 months after the final treatment because the treatment period was long), the following items were evaluated on the basis of the criteria, and the evaluation was shown in points in terms of the objective symptoms and subjective symptoms. Besides, the side effects were also observed and shown in points as shown hereinafter. Global evaluation was done in the sum of these points on the basis of global evaluation criteria.

The patient No. 5 was externally injured during the treatment and inflammation was observed on the surface of keloid, and hence, the treatment was stopped after treatment for one month and one week. Thus, this patient was excluded from the evaluation as a dropped-out case.

(a) Evaluation items and criteria of the therapeutic effects during the administration of test preparation:

a-1) Evaluation items and criteria of objective symptoms:

Four items of height, area, color and hardness of keloid were evaluated by the following criteria.

Improvement was observed within one week after initiation of the treatment . . . Point 2

Improvement was observed within two weeks after initiation of the treatment . . . Point 1

No improvement was observed during treatment or improvement was observed after two weeks of initiation of the treatment . . . Point 0

Keloid took a turn for the worse . . . Point −1 a-2) Evaluation items and criteria of subjective symptoms:

The patients were asked as to three items of pain, pruritus and feeling of hardened skin, and the evaluation points were shown in the same criteria and points as in the above objective symptoms. However, the infant patient (patient No. 1) could hardly reply to such questions, and hence, the evaluation was omitted.

(b) Evaluation items and criteria of the therapeutic effects 6 months (2 months as to patient No. 9) after the final administration of test preparation:

b-1) Evaluation items and criteria of objective symptoms:

The same four items as in the above evaluation during the treatment were evaluated likewise, provided that the criteria and points were as follows.

Improvement effects on the last day of treatment were maintained . . . Point 2

Improvement effects on the last day of treatment were somewhat decreased but the improvement was still observed in comparison with the state before the treatment . . . Point 1

No change was observed in comparison with the state before the treatment . . . Point 0

Keloid took a turn for the worse than the state before the treatment . . . Point −1 b-2) Evaluation items and criteria of subjective symptoms:

The same three items as in the evaluation during the treatment were evaluated, except that the criteria and points were the same as in the above b-1).

(c) Evaluation method and criteria of side effects:

When any symptoms of objective side effects and subjective side effects were observed during the treatment and 6 months (2 months as to patient No. 9) after the final treatment, the symptom was recorded. Each symptom of side effect was given a point (−1), and the points were summed. When no side effect was observed, it was evaluated as point: 0.

(d) Global evaluation criteria:

Whole evaluation points for therapeutic effects and points of the side effects during the treatment and 6 months (2 months as to patient No. 9) after the final treatment were summed in each patient, and based on the thus obtained total evaluation points and the following global evaluation criteria, the effects were classified in four degrees of from "markedly useful" to "undesirable" as shown below. However, in the infant patient, since the evaluation of subjective symptom was omitted, the sum of the evaluation points in the objective symptom was taken as the total evaluation points, and based on the total evaluation points and the following global evaluation criteria for infant, the effects were classified in four degrees of from "markedly useful" to "undesirable".

[Global evaluation criteria]:

Total points 18 or more . . . markedly useful
Total points 13–17 . . . useful
Total points 4–12 . . . slightly useful
Total points 0–3 . . . not useful
Total point −1 or less . . . undesirable Global evaluation criteria for infant]:

Total points 8 or more . . . markedly useful
Total points 4–7 . . . useful
Total points 1–3 . . . slightly useful
Total points 0 . . . not useful
Total point −1 or less . . . undesirable 5. Test results:

Each evaluation points and global evaluation results are shown in Table 2. Since the data of the patient No. 5 were omitted as a dropped-out case, the data are not shown in Table 2.

TABLE 2

| | Evaluation during treatment | | | | | | | |
|---|---|---|---|---|---|---|---|---|
| | Therapeutic effects | | | | | | | |
| | Evaluation of objective symptoms | | | | Evaluation of subjective symptoms | | | |
| Patient No.[a)] | Height | Area | Color | Hardness | Pain | Pruritus | Feeling of hardened skin | Side effects |

TABLE 2-continued

| 1 | 2 | 1 | 1 | 1 | c) | c) | c) | 0d) |
|---|---|---|---|---|----|----|----|----|
| 2 | 2 | 1 | 1 | 1 | 1  | 1  | 2  | 0  |
| 3 | 1 | 1 | 1 | 1 | 1  | 1  | 2  | 0  |
| 4 | 2 | 2 | 1 | 1 | 1  | 1  | 2  | 0  |
| 6 | 1 | 1 | 1 | 2 | 1  | 1  | 1  | 0  |
| 7 | 2 | 1 | 1 | 1 | 1  | 1  | 1  | 0  |
| 8 | 1 | 1 | 1 | 1 | 1  | 1  | 2  | 0  |
| 9 | 2 | 2 | 2 | 2 | 2  | 2  | 2  | 0  |

| | Evaluation 6 months[b] after the final treatment | | | | | | | |
|---|---|---|---|---|---|---|---|---|
| | Therapeutic effects | | | | | | | |
| | Evaluation of objective symptoms | | | | Evaluation of subjective symptoms | | | |
| Patient No.[a] | Height | Area | Color | Hardness | Pain | Pruritus | Feeling of hardened skin | Side effects | Total points | Global Evaluation |
| 1 | 0 | 0 | 0 | 0 | c) | c) | c) | 0d) | 5d) | Useful[d] |
| 2 | 2 | 1 | 1 | 1 | 1 | 1 | 2 | 0 | 18 | Markedly useful |
| 3 | 1 | 1 | 1 | 1 | 1 | 1 | 2 | 0 | 16 | Useful |
| 4 | 2 | 2 | 2 | 2 | 1 | 1 | 1 | 0 | 21 | Markedly useful |
| 6 | 1 | 1 | 1 | 2 | 1 | 1 | 1 | 0 | 16 | Useful |
| 7 | 2 | 2 | 2 | 2 | 1 | 1 | 1 | 0 | 19 | Markedly useful |
| 8 | 2 | 1 | 1 | 1 | 1 | 1 | 2 | 0 | 17 | Useful |
| 9 | 2 | 2 | 2 | 2 | 2 | 2 | 2 | 0 | 28 | Markedly useful |

[Note]
[a] The data of patient No. 5 were not described because of dropped-out case
[b] In patient No. 9, the evaluation was after 2 months
[c] Unable to evaluate because of infant
[d] The evaluation was done on the basis of global evaluation criteria for infant As is shown in Table 2, the treating agent of the present invention was effective in all evaluation items during the treatment and showed particularly high effects in decrease of height of keloid and feeling of hardened skin.

Even 6 months (2 months in patient No. 9) after the final treatment, the treating agent of the present invention did not show any rebound phenomenon even by stopping of administration of the agent, which is a particularly characteristic effect of the treating agent of the present invention.

On the other hand, the treating agent of the present invention did not show any side effect unless the keloid had external injury. In patient No. 5, an inflammation was observed, but it is assumed to be due to the external injury.

According to the global evaluation, the treating agent of the present invention was "useful" or "markedly useful" in all 8 patients, wherein the evaluation "useful" was in four patients and the evaluation "markedly useful" was in four patients.

Thus, the agent of the present invention is very excellent for the treatment of keloid.

Test 2

1. Test preparation:
   (i) The ointment of Example 2
   (ii) A steroid ointment (triamcinolone acetonide ointment) (as a reference ointment)

2. Patient to be treated:
The patient was a male patient (age, 34 old years) who was suffered from a hypertrophic scar (length about 10 cm, width about 1.5 cm, height about 0.3 cm) produced by operation on a stomach ulcer, said operation having been done 6 years and 4 months previously.

3. Test method:
A cross-over trial was done in comparison with the reference steroid ointment (triamcinolone acetonide ointment). For the first one month, the triamcinolone acetonide ointment was applied to the keloid region in a dose of 50 $\mu g/cm^2$ (skin area) (as triamcinolone acetonide) once a day. After wash-out period of two weeks, the ointment of Example 2 was applied to in the same manner as above in a dose of 10 $\mu g/cm^2$ (skin area) (as ethanolamine) once a day for one month.

4. Evaluation of the therapeutic effects:
(1) Evaluation items and evaluation criteria:
During the administration with each test material, the therapeutic effects were evaluated by the same evaluation items and evaluation criteria as in the above test 1.

(2) Method for global evaluation:
The evaluation points in all evaluation items were summed, and based on the thus obtained total evaluation points the effects were classified in four degrees of from "markedly useful" to "undesirable" by the following global evaluation criteria.

[Global evaluation criteria]:

Total points 9 or more . . . markedly useful
Total points 5-8 . . . useful
Total points 1-4 . . . slightly useful
Total points 0 . . . not useful
Total points −1 or less . . . undesirable 4. Test results:
Each evaluation points and global evaluation results are shown in Table 3.

TABLE 3

| | Test materials used | |
|---|---|---|
| Evaluation items | Ointment of Example 2 | Steroid ointment |
| Objective symptoms: | | |
| Height | 2 | 0 |
| Area | 2 | 0 |
| Color | 2 | 0 |
| Hardness | 2 | 0 |
| Subjective symptoms: | | |
| Pain | 2 | 0 |
| Pruritus | 2 | 0 |
| Feeling of Hardened skin | 2 | 0 |
| Side effect | 0 | 0 |
| Total evaluation points | 14 | 0 |
| Global evaluation | Markedly useful | Not useful | evaluated to be not useful because no improvement was observed in either objective symptoms or in subjective symptoms.

On the contrary, the ointment of Example 2 was effective in all evaluation items, and particularly, the pruritus disappeared immediately after initiation of the treatment and no side effect was observed, and the global evaluation was "markedly useful". Thus, the treating agent of the present invention was superior to the reference steroid ointment.

Test 3

Skin irritation test (patch test)
1. Test preparation:
   A 1% aqueous solution of ethanolamine hydrochloride.
2. Person to be tested:
   Normal adults, 19 persons
3. Test method:
   According to a closed-patch test, the test material was occlusively applied to the forearm of the persons to be tested in a dose of 0.05 ml for 24 hours with KI chamber (cf. Journal of the Society of Cosmetic Chemist, Vol. 31, page 97, 1980), and thereafter the patch was removed. At one hour and 24 hours after removal of the patch, the reaction on the skin was observed.
4. Test results:
   At one hour and 24 hours after removal of the patch, a slight erythema was observed in one person, but no irritation was observed in other persons. Thus, it was evaluated that the agent of the present invention has almost no irritation to the skin.

EXAMPLES

The preparation of the treating agent of the present invention is illustrated by the following examples.

EXAMPLE 1

Ethanolamine hydrochloride (100 mg) and the following hydrophilic components are mixed with heating at 80° C. on a water bath, and the mixture is gradually added to the following lipophilic components warmed at 80° C. with stirring. The mixture is vigorously stirred for 2.5 minutes at 2500 r.p.m. with a homogenizer (manufactured by Tokusyukika Kogyo Co., Ltd.) so that each components are well emulsified. The mixture is gradually cooled with stirring to give an ointment containing ethanolamine hydrochloride of 100 mg per 100 g of the ointment.

| [Hydrophilic components] | |
| --- | --- |
| Methyl parahydroxybenzoate | 0.1 g |
| Propylene glycol | 6.7 g |
| Purified water | 44.0 g |
| [Lipophilic components] | |
| Squalane | 4.7 g |
| White petrolatum | 24.0 g |
| Stearyl alcohol | 8.7 g |
| Isopropyl myristate | 6.0 g |
| Polyethylene glycol monostearate (tradename NIKKOL MYS-45, manufactured by Nihon Surfactant Kogyo K.K.) | 1.3 g |
| Polyoxyethylene alkyl ether phosphate (tradename NIKKOL DDP-2, manufactured by Nihon Surfactant Kogyo K.K.) | 2.3 g |
| Glyceryl monostearate | 2.0 g |
| Butyl parahydroxybenzoate | 0.1 g |

EXAMPLE 2

In the same manner as described in Example 1 by using ethanolamine hydrochloride (500 mg) and the following hydrophilic components and lipophilic components there is prepared an ointment containing ethanolamine hydrochloride of 500 mg per 100 g of the ointment.

| [Hydrophilic components] | |
| --- | --- |
| Methyl parahydroxybenzoate | 0.1 g |
| Propylene glycol | 6.7 g |
| Purified water | 43.6 g |
| [Lipophilic components] | |
| Squalane | 4.7 g |
| White petrolatum | 24.0 g |
| Stearyl alcohol | 8.7 g |
| Isopropyl myristate | 6.0 g |
| Polyethylene glycol monostearate (tradename NIKKOL MYS-45, manufactured by Nihon Surfactant Kogyo K.K.) | 1.3 g |
| Polyoxyethylene alkyl ether phosphate (tradename NIKKOL DDP-2, manufactured by Nihon Surfactant Kogyo K.K.) | 2.3 g |
| Glyceryl monostearate | 2.0 g |
| Butyl parahydroxybenzoate | 0.1 g |

EXAMPLE 3

In the same manner as described in Example 1 by using ethanolamine hydrochloride (100 mg) and the following hydrophilic components and lipophilic components there is prepared a lotion containing ethanolamine hydrochloride of 100 mg per 100 g of the lotion.

| [Hydrophilic components] | |
| --- | --- |
| Sodium lauryl sulfate | 0.5 g |
| Purified water | 92.8 g |
| [Lipophilic components] | |
| Bleached beeswax | 0.1 g |
| Cetanol (tradename VINASOL NAA 48, manufactured by Nippon Oil & Fats Co. Ltd.) | 1.5 g |
| Glycerin, concentrated | 5.0 g |

What is claimed is:

1. A method for the treatment of keloid, which comprises topically administering to a patient suffering from keloid an amount of ethanolamine or a pharmaceutically acceptable salt thereof effective for the treatment of keloid.

2. The method of claim 1, wherein the ethanolamine or salt thereof is administered in an amount of 0.2–1000 $\mu g/cm^2$ or skin area per administration.

3. The method of claim 2, wherein the amount is 2–1000 $\mu g/cm^2$ of skin area per administration.

4. The method of claim 1, wherein the ethanolamine or salt thereof is administered in the form of a pharmaceutical preparation selected from the group consisting of an ointment, a gel preparation, a cream, a liquid, a spray, a patch and a lotion, the preparation comprising the ethanolamine or salt thereof, in an amount effective for treatment of keloid and a topical carrier.

5. The method of claim 4, wherein the ethanolamine or salt thereof is present in the preparation in an amount of 0.01–20% by weight based on the weight of the preparation.

* * * * *

UNITED STATES PATENT AND TRADEMARK OFFICE
CERTIFICATE OF CORRECTION

PATENT NO. : 5,128,375

DATED : July 7, 1992

INVENTOR(S) : Masaya TANAKA et al.

It is certified that error appears in the above-identified patent and that said Letters Patent is hereby corrected as shown below:

Column 8, line 54:
Claim 2, line 3, change "or skin" to --of skin--.

Signed and Sealed this

Twenty-third Day of November, 1993

*Attest:*

BRUCE LEHMAN

*Attesting Officer*     *Commissioner of Patents and Trademarks*